(12) United States Patent
Kanarowski et al.

(10) Patent No.: US 10,352,860 B2
(45) Date of Patent: Jul. 16, 2019

(54) SUPER RESOLUTION MICROSCOPY

(71) Applicant: Bruker Nano, Inc., Santa Barbara, CA (US)

(72) Inventors: Stan Kanarowski, Santa Barbara, CA (US); Eyal Shafran, Santa Barbara, CA (US)

(73) Assignee: Bruker Nano, Inc., Billerica, MA (US)

( * ) Notice: Subject to any disclaimer, the term of this patent is extended or adjusted under 35 U.S.C. 154(b) by 0 days.

(21) Appl. No.: 15/306,357

(22) PCT Filed: Apr. 24, 2015

(86) PCT No.: PCT/US2015/027676
§ 371 (c)(1),
(2) Date: Oct. 24, 2016

(87) PCT Pub. No.: WO2015/164844
PCT Pub. Date: Oct. 29, 2015

(65) Prior Publication Data
US 2017/0276608 A1    Sep. 28, 2017

Related U.S. Application Data

(60) Provisional application No. 61/983,931, filed on Apr. 24, 2014.

(51) Int. Cl.
*G01N 21/64* (2006.01)
*G02B 21/00* (2006.01)
*G02B 27/58* (2006.01)

(52) U.S. Cl.
CPC ..... *G01N 21/6458* (2013.01); *G01N 21/6428* (2013.01); *G02B 21/008* (2013.01);
(Continued)

(58) Field of Classification Search
CPC ........... G01N 21/6428; G01N 21/6458; G01N 2021/6417; G01N 21/645;
(Continued)

(56) References Cited

U.S. PATENT DOCUMENTS 5,283,684 A    2/1994 Thomas et al.
5,717,519 A *  2/1998 Sugiyama .......... G02B 21/0024
                                                    359/234
(Continued)

FOREIGN PATENT DOCUMENTS

EP    0 539 691 B1    10/1997
EP    1 538 470 A2    6/2005
(Continued)

OTHER PUBLICATIONS

Bewersdorf et al, "Multifocal Multi-Photon Microscopy" Handbook of Biological Confocal Microscopy; Springer; 2006; vol. 23 Issue 9; Chapter 29; pp. 550-560.
(Continued)

*Primary Examiner* — Taeho Jo
(74) *Attorney, Agent, or Firm* — Thorpe North & Western, LLP

(57) ABSTRACT

A super resolution microscope system is disclosed and described. The system can include a sample stage (180) adapted to receive a sample (185) including probe molecules. At least one light source (105) is provided to produce a coherent excitation light to excite the probe molecules and cause luminescence of the probe molecules. An image detector (100) can detect the luminescence from the probe molecules. A microlens array (125) can be positioned in a beam path (110) of the coherent light from the at least one light source (105). The beam path (110) of the coherent light extends between the light source (105) and the sample stage (180). The microlens array (125) can also be positioned in a
(Continued)

beam path (112) of the luminescence from the probe molecules. The beam path (112) of the luminescence extends between the sample stage (180) and the image detector (100).

16 Claims, 9 Drawing Sheets

(52) U.S. Cl.
CPC ..... *G02B 21/0032* (2013.01); *G02B 21/0044* (2013.01); *G02B 21/0076* (2013.01); *G02B 27/58* (2013.01); *G01N 21/6445* (2013.01); *G01N 2021/6439* (2013.01); *G01N 2021/6471* (2013.01); *G01N 2021/6478* (2013.01); *G01N 2201/067* (2013.01)

(58) Field of Classification Search
CPC ... G01N 2021/6478; G01N 2021/6471; G01N 21/6445; G01N 21/6452; G01N 2021/6439; G01N 2201/067; G02B 21/0032; G02B 21/0044; G02B 21/0076; G02B 21/008; G02B 27/58
USPC ...................................... 250/459.1
See application file for complete search history.

(56) References Cited

U.S. PATENT DOCUMENTS

| | | | |
|---|---|---|---|
| 5,969,846 A | 10/1999 | Kishi | |
| 6,028,306 A | 2/2000 | Hayashi | |
| 6,191,885 B1 | 2/2001 | Kitagawa | |
| 6,749,346 B1 | 6/2004 | Dickensheets et al. | |
| 6,750,963 B2 | 6/2004 | Sampas | |
| 6,838,650 B1* | 1/2005 | Toh | G02B 21/0024 250/201.3 |
| 7,088,487 B2 | 8/2006 | Lauer | |
| 7,095,556 B2* | 8/2006 | Iketaki | G02B 26/08 250/458.1 |
| 7,190,514 B2 | 3/2007 | Mikuriya et al. | |
| 7,400,446 B2 | 7/2008 | Mikuriya et al. | |
| 7,446,957 B2 | 11/2008 | Tanaami et al. | |
| 7,474,403 B2 | 1/2009 | Muller et al. | |
| 7,586,086 B2 | 9/2009 | Lauer | |
| 7,598,502 B2 | 10/2009 | Nishiwaki et al. | |
| 7,599,113 B2 | 10/2009 | Tanibata et al. | |
| 7,808,700 B2 | 10/2010 | Hirukawa et al. | |
| 8,275,226 B2 | 9/2012 | Berman | |
| 8,643,947 B2 | 2/2014 | Nezu et al. | |
| 8,705,172 B2 | 4/2014 | Kleppe et al. | |
| 8,922,887 B2 | 12/2014 | Cooper | |
| 9,250,185 B2* | 2/2016 | Sirat | G02B 21/0056 |
| 2005/0111089 A1 | 5/2005 | Baer | |
| 2006/0012872 A1* | 1/2006 | Hayashi | G01N 21/21 359/386 |
| 2006/0072191 A1 | 4/2006 | Akiyama et al. | |
| 2006/0147176 A1* | 7/2006 | Takamatsu | G02B 21/14 385/147 |
| 2007/0146869 A1 | 6/2007 | Lauer | |
| 2007/0154938 A1* | 7/2007 | Oshida | G01N 21/6428 435/6.11 |
| 2010/0067103 A1* | 3/2010 | Sangu | G02B 21/16 359/385 |
| 2010/0142041 A1* | 6/2010 | Berman | G02B 21/0032 359/385 |
| 2011/0090553 A1 | 4/2011 | Kei | |
| 2011/0297847 A1 | 12/2011 | Courtney et al. | |
| 2012/0081535 A1* | 4/2012 | Hayashi | G02B 21/0032 348/79 |
| 2012/0281258 A1* | 11/2012 | Sheblee | G02B 21/0044 358/474 |
| 2013/0010098 A1* | 1/2013 | Kalkbrenner | G01N 21/6428 348/79 |
| 2013/0010353 A1* | 1/2013 | Berman | G02B 21/0032 359/385 |
| 2013/0128346 A1* | 5/2013 | Sanguu | G02B 21/06 359/385 |
| 2013/0235255 A1 | 9/2013 | Westphal et al. | |
| 2014/0104681 A1 | 4/2014 | Berman | |
| 2014/0192406 A1 | 7/2014 | Bathe | |
| 2015/0085289 A1* | 3/2015 | Kang | G02B 21/004 356/445 |
| 2015/0131148 A1* | 5/2015 | Redford | G02B 21/0032 359/389 |
| 2015/0168702 A1* | 6/2015 | Harris | G02B 21/08 850/30 |
| 2015/0177503 A1 | 6/2015 | Sangu | |
| 2015/0234178 A1 | 8/2015 | Azuma | |
| 2016/0161728 A1* | 6/2016 | Sangu | G02B 21/0044 359/203.1 |
| 2016/0238827 A1* | 8/2016 | Shroff | G02B 21/0032 |

FOREIGN PATENT DOCUMENTS

| | | |
|---|---|---|
| WO | WO 2014/005195 A2 | 1/2014 |
| WO | WO 2014/070912 A1 | 5/2014 |
| WO | WO 2014/114702 A1 | 7/2014 |

OTHER PUBLICATIONS

Fujita et al, "Confocal Multipoint Multiphoton Excitation Microscope With Microlens and Pinholes Arrays" Optics Communications; Elsevier; Jan. 15, 2000; vol. 174 Issue 1-4.

Habaza et al, "Tomographic Phase Microscopy With 180 Degree Rotation of Live Cells in suspension by Holographic Optical Tweezers" Optics Letters; Optical Society of America; Apr. 15, 2015; vol. 40 Issue 8; pp. 1881-1884.

PCT Application No. PCT/US15/27676; Filing Date Apr. 24, 2015, Stan Kanarowski, International Search Report, dated Aug. 4, 2015, 10 Pages.

Sisan et al, "Spatially Resolved Fluorescence Correlation Spectroscopy Using a Spinning Disk Confocal Microscope" Biophysical Journal; Biophysical Society; Dec. 2006; vol. 91; pp. 4241-4252.

Takai et al, "Confocal Scanner System for Long-term Live Cell Imaging" Yokogawa Technical Report English Edition; 2012; vol. 55 Issue 1; pp. 27-30.

* cited by examiner

SUPER RESOLUTION MICROSCOPY

RELATED APPLICATION(S)

This application claims the benefit of U.S. Provisional Patent Application Ser. No. 61/983,931, filed on Apr. 24, 2014, the entire contents of which are incorporated herein by reference.

FIELD OF THE INVENTION

This invention relates to microscopy. More specifically, the invention relates to super resolution microscopy and the creation of images obtainable therewith. Therefore, the present invention relates generally to the fields of physics, optics, chemistry and biology.

BACKGROUND

Until about a decade ago, resolution in far-field light microscopy was thought to be limited to 200-280 nanometers in the focal plane, concealing details of sub-cellular structures and constraining its biological applications. Breaking this diffraction barrier by the seminal concept of stimulated emission depletion ("STED") microscopy has made it possible to image biological systems at the nanoscale with light. STED microscopy and other members of reversible saturable optical fluorescence transitions ("RESOLFT") family achieve a resolution greater than 10-fold beyond the diffraction barrier by engineering the microscope's point-spread function ("PSF") through optically saturable transitions of the (fluorescent) probe molecules.

Current understanding of fundamental biological processes on the nanoscale (e.g., neural network formation, chromatin organization) is limited because these processes cannot be visualized, at a sub diffraction resolution, for an extended period, at imaging depths up to 50 microns. Current biological research at the sub-cellular level is constrained by the limits of spatial and temporal resolution in fluorescence microscopy. The diameter of most organelles is below the diffraction limit of light, limiting spatial resolution and concealing sub-structure. Although recent developments have improved spatial resolution and even overcome the traditional diffraction barriers, comparable improvements in temporal resolution are still needed.

Particle-tracking techniques can localize small objects (typically less than the diffraction limit) in live cells with sub-diffraction accuracy and track their movement over time. But conventional particle-tracking fluorescence microscopy cannot temporally resolve interactions of organelles, molecular machines, or even single proteins, which typically happen within milliseconds. The spatial localization accuracy of single particles in a fluorescence microscope is approximately proportional to spatial resolution divided by the total number of detected fluorescence photons from the particle in the absence of background and effects due to finite pixel size. For longer acquisition times more signal can be accumulated, hence increased temporal resolution requires a trade-off of decreased spatial localization accuracy.

SUMMARY

Thus, there is a need for a microscopy system that can provide super resolution imaging with sub diffraction resolution in all three dimensions. Another need is directed to live cell tracking over extended periods of time without bleaching. The present invention is directed to satisfying one or more of these needs and solving other problems.

In light of the problems and deficiencies noted above, the present invention provides microscopy systems and methods for creating images using probe molecules. In accordance with one embodiment, a super resolution microscope system is provided. The system includes a sample stage adapted to receive a sample. The system includes at least one light source configured to produce a coherent excitation light and cause luminescence of probe molecules in the sample. The system includes an image detector configured to detect the luminescence from the probe molecules. The system also includes a microlens array. The microlens array is positioned in a beam path of the coherent light from the at least one light source. The beam path of the coherent light extends between the at least one light source and the sample stage. The microlens array is also positioned in a beam path of the luminescence from the probe molecules. The beam path of the luminescence extends between the sample stage and the image detector.

In a more detailed example, the microlens array is arranged on a microlens disk which is adapted to connect to a motor and is configured to rotate.

In a more detailed example, the microlens array includes a plurality of converging lenses and a plurality of diverging lenses. The microlens array is positioned to transmit the coherent light through the plurality of converging lenses and to transmit the luminescence through the plurality of diverging lenses.

In a more detailed example, the microlens array is attached to a motor and is configured to be shaken while transmitting the coherent light and the luminescence.

In a more detailed example, the system includes a pinhole array oriented in at least one of the beam path of the coherent light and the beam path of the luminescence. The pinhole array is arranged on a pinhole disk attached to a motor and is configured to rotate or is configured to be shaken.

In a more detailed example, a dichroic mirror is positioned between the microlens array and the pinhole array. The dichroic mirror is configured to receive the coherent light from a direction parallel with a plane of the microlens array and a plane of the pinhole array. The dichroic mirror is configured to reflect the coherent light through the microlens array. The dichroic mirror is further configured to transmit the luminescence from the microlens array to the pinhole array.

In a more detailed example, the microlens array is arranged in a circular pattern and the pinhole array is arranged in a semi-circular pattern corresponding to approximately one half of the circular pattern of the microlens array.

In a more detailed example, the microlens array and the pinhole array are arranged on a common disk.

In a more detailed example, the pinhole array and microlens array are oriented on a common disk and contact one another in a layered configuration.

In a more detailed example, the microlens array is positioned in a beam path of the luminescence such that the beam path of the luminescence passes through the microlens array twice between the sample stage and the image detector.

In a more detailed example, the system includes a prism positioned on one side of the microlens array. The prism is configured to transmit the coherent light from the one side of the microlens array to the microlens array toward the sample stage along the beam path of the coherent light. The prism is further configured to receive the luminescence from the microlens array and reflect the luminescence back toward the microlens array.

In a more detailed example, the beam path of the luminescence passes through only a single microlens array.

In a more detailed example, the microlens array is a first microlens array and the system further includes a second microlens array positioned in the beam path of the coherent light from the at least one light source. The system further includes a pinhole array positioned in the beam path of the coherent light and in the beam path of the luminescence. The system further includes a dichroic mirror positioned between the first and second microlens arrays to redirect the luminescence from the first microlens array toward the image detector and away from the second microlens array.

In a more detailed example, the system includes a motor coupled to the microlens array and configured to move the microlens array with respect to the beam paths of the coherent light and the luminescence.

In one example, a method for performing super resolution microscopy is provided. The method includes mounting a sample on a sample stage, the sample having a plurality of probe molecules. The method includes switching on a light source configured to produce a coherent excitation light to cause the coherent light to pass through a microlens array positioned in a beam path extending between the light source and the sample stage. The method includes illuminating the sample with coherent light to cause luminescence from the probe molecules in the sample to pass through the microlens array positioned in a beam path between the sample stage and an image detector. The method includes detecting the luminescence from the probe molecules at the image detector.

In a more detailed example, the method includes rotating the microlens array while illuminating the sample.

In a more detailed example, the method includes rotating a pinhole array oriented in the beam path between the sample stage and the image detector in synchronization with rotating the microlens array.

In a more detailed example, the microlens array is arranged in a circular pattern and the pinhole array is arranged in a semi-circular pattern. The method further includes switching the light source off when the pinhole array is rotated in the beam path between the light source and the sample stage and switching the light source on when the pinhole array is rotated out of the beam path between the light source and the sample stage.

In a more detailed example, the method includes detecting the luminescence from the at least one subset of probe molecules at the image detector when the pinhole array is rotated out of the beam path between the light source and the sample stage.

In a more detailed example, the method includes directing the coherent light from the light source toward a dichroic mirror between the microlens array and the pinhole array to be redirected toward the sample stage.

In a more detailed example, the method includes detecting the luminescence from the at least one subset of probe molecules at the image detector after the luminescence has passed through both the microlens array and the pinhole array.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

Figure 1:
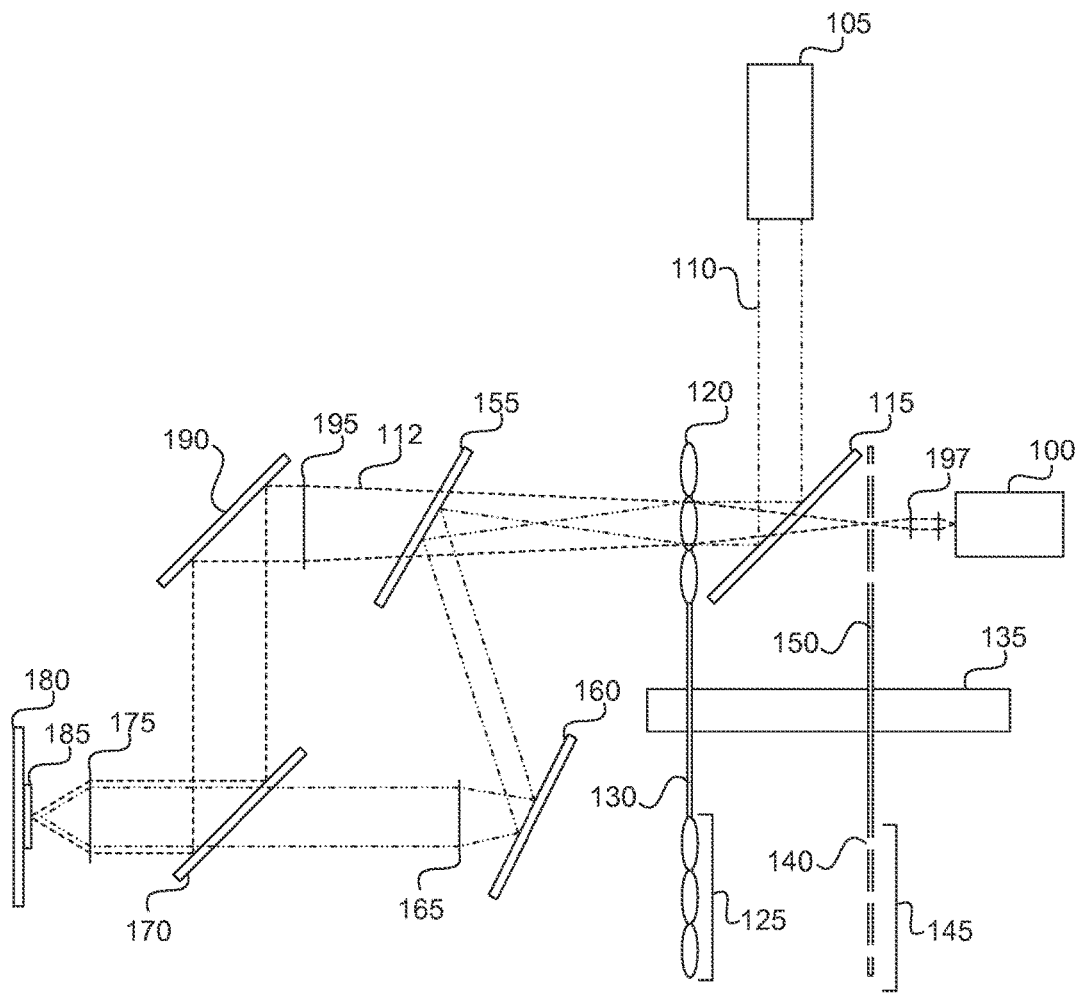
FIGS. 1-2 are schematic views of a super resolution microscopy system in accordance with examples of the present technology.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a particle" includes reference to one or more of such materials and reference to "subjecting" refers to one or more such steps.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, or only C, and combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Embodiments of the Invention

The invention provides for acquisition of super resolution images of fluorescent proteins. The system may provide image acquisition of both biological and material samples at resolutions far below standard instrumentation. More specifically, this invention is an improvement to recent developments in multi-focal structured illumination microscopy (i.e. MSIM or analog-SIM). Thus, the underlying physics and design of such systems are known and described in various references such as: York et al., "*Resolution doubling in live, multicellular organisms via multifocal structured illumination microscopy,*" Nat. Methods 9(7), 749-754 (2012), 10.1038/nmeth.2025; York et al., "*Instant super-resolution imaging in live cells and embryos via analog image processing,*" Nat. Methods 10(11), 1122-6 (2013), 10.1038/nmeth.2687; Sheppard, C. J. R., "*Super-resolution in Confocal Imaging,*" Optik 80, no. 2, 53-54 (1998); Roth et al., "*Optical Photon Reassignment Microscopy,*" arXiv: 1306.6230 [physics.optics] (2013); De Luca et al., "*Re-scan confocal microscopy: scanning twice for better resolution,*" Biomed Opt Express 4(11), 2644-2656 (2013); Schulz et al., "*Resolution doubling in fluorescence microscopy with confocal spinning-disk image scanning microscopy,*" Proc Nat Acad Sci vol. 110, no. 52, 21000-21005 (2013), 10.1073/pnas.1315858110, and Shroff et al., International Patent Application Publication No. WO 2013/126762, which are each incorporated in their entireties as if fully reproduce herein.

In accordance with an embodiment shown in FIG. 1, a super resolution microscopy system is provided. The system can include a sample stage 180 adapted to receive a sample 185 including probe molecules. At least one light source 105 is provided to produce a coherent excitation light beam 110 to excite the probe molecules and cause luminescence of the probe molecules. An image detector 100 can detect the luminescence from the probe molecules. A microlens array 125 can be positioned in an excitation beam path 110 of the coherent light from the at least one light source 105. The beam path 110 of the coherent light extends between the light source 105 and the sample stage 180. The microlens array 125 can also be positioned in an emission beam path 112 of the luminescence from the probe molecules. In order to implement the invention while also preserving MSIM principles, the emissions microlens array can be oriented at a distance within 30% of one focal length before a focus formed by the tube lens which produces an emission foci with up to doubled sharpness, which enhances resolution improvement up to a square root of two before processing. Typically, this will be about 0.75 to 1.3 times the focal length, although in some cases can be about 0.9 to about 1.1 times the focal length. The beam path 112 of the luminescence extends between the sample stage 180 and the image detector 100.

The present microscopy system can further include a microlens disk 130 upon which the microlens array 125 is arranged, an optional pinhole array 145 including pinholes 140 arranged on a pinhole disk 150, and a rotating unit (e.g., drum 135 coupled to a motor, not shown) adapted to rotate the microlens array 125 and optionally to synchronously rotate the pinhole array 145. The microlens array 125 includes a plurality microlenses 120 arranged in a pattern. The pinhole array 145 includes a plurality of pinholes 140 that are arranged in a similar or same pattern as that of the microlenses 120 in the microlens array 125. Although optional, the pinhole array can eliminate or reduce out of focus light by sectioning which can further improve resolution. The microlens disk 130 and the pinhole disk 150, when used in combination, may optionally be separated by a defined distance. The rotating unit (e.g., drum 135) can integrally rotate the microlens disk 130 and the pinhole disk 150.

The microlens disk 130 and/or the pinhole disk 150 can be Nipkow-type scanning disks. The pattern of arrangement of the microlenses 120 and the pinholes 140 can be in a spiral pattern or other suitable pattern. (FIG. 4B described below illustrates an example non-spiral pattern). The microlenses 120 on the microlens disk 130 and the pinholes 140 on the pinhole disk 150 can be aligned and in a fixed position relative to one another. The arrangement of the microlenses 120 can facilitate scanning of images.

The present system is a laser scan confocal microscopy system with a multi-foci arrangement, configured to perform multiple scans of light to yield super resolution. Whereas previous super resolution technologies for imaging provided comparatively low imaging speeds or high photo-toxicity, the present technology enables high resolution imaging at high speeds with efficient, compact designs and low photo-toxicity. For example, the system can include a microlens array 125 in the excitation beam path 110 and a microlens array 125 and pinhole array 145 in the emission beam path 112, where the microlens array in the excitation path and the emission path can be the same microlens array 125.

FIG. 1 illustrates the excitation beam path 110 originating at a light source 105. The light source 105 can be a coherent light source, such as a laser. The light source 105 can include a plurality of light sources, and each of the plurality of light sources can produce a different wavelength of light. The light produced by the light source 105 can be an excitation beam 110.

The excitation beam path 110 continues from the light source 105 to a dichroic mirror 115 positioned between the microlens array 125 and the pinhole array 145. While FIG. 1 and other figures herein illustrate a single dichroic mirror 115 extending across a height of a plurality of the microlenses or pinholes, any number of one or more dichroic mirrors of a suitable size may be positioned between the microlens 130 and pinhole disks 150 to redirect the excitation beam 110. The dichroic mirror(s) 115 can be stationary relative to rotating or otherwise moving microlens 130 and pinhole disks 150. The excitation beam 110 is redirected through the microlens array 125 toward the sample 185 on the sample stage 180. For example, the microlens array 125 in FIG. 1 directs the excitation beam 110 toward dichroic mirror 155, which redirects the excitation beam 110 toward mirror 160, which directs the excitation beam 110 to the sample 185, passing through dichroic mirror 170. (The dichroic mirror 170 may optionally be replaced with a dichroic beam cube). The excitation beam 110 redirected from mirror 160 can pass through a tube lens 165 and be collimated. A microscope objective 175 can focus the excitation beam 110 onto the sample 185 on the sample stage 180.

The excitation beam 110 can excite probe molecules in the sample 185 and cause the probe molecules to luminesce. The luminescence can be light emitted from the probe molecules and can follow an emission beam path 112 or luminescence path towards an imaging device 100, such as a camera. In FIG. 1, the emission beam path 112 is directed from the microscope objective 175 toward dichroic mirror 170, and redirected to mirror 190. Mirror 190 can reflect the emission beam 112 toward a tube lens 195 which focuses the emission beam 112 toward the microlens array 125. One or more microlenses 120 in the microlens array can further focus the emission beam 112 to pass through dichroic mirror 115 and through the pinholes 140 in the pinhole array 145. The emission beam 112 can be directed toward the imaging device 100 after passing through the pinhole array 145. Additional optics 197 can be included between the pinhole array 145 and the imaging device 100 to shape, focus, redirect or otherwise treat the emission beam 112. As an alternative configuration (not shown), tube lens 195 may be omitted and tube lens 165 can be moved from between mirror 160 and dichroic mirror 170 to a position in the excitation beam 110 between dichroic mirror 170 and the objective 175.

In order to achieve super resolution, the same microlens array 125 is used for both the excitation path 110 and emission path 112. Doing so eliminates the need for a second microlens array, such as a negative microlens disk. FIG. 1 illustrates decoupling of the excitation 110 and emission beam paths 112 using dichroic mirrors 115, 155, 170 and placing a different tube lens 165, 195 in each path. The excitation tube lens 165 can be placed a further distance ($d_{ex}$ or $d_{em}$) away from the microlenses 120 ($d_{ex}=f_{TL}+f_{ML}$) than the emission tube lens 195 ($d_{em}=f_{TL}-f_{ML}$), where $f_{TL}$ is the focal distance of the tube lens and $f_{ML}$ is the focal distance of the microlens array. The local magnification of the emission is doubled due to the placement of the emission tube lens 195 in relation to the microlens array. A second optional pinhole disk can be used in order to improve sectioning of the emission beam.

Using the same microlens disk 130 twice greatly reduces complexity in the number of parts, the alignment of parts, the cost of the system, and so forth. For example, if the emission path passes through two different sets of microlenses (e.g., positive and negative) a very high level of fabrication accuracy may be required to position each positive lens very precisely with respect to a negative lens. According to the present technology, since the excitation and emission beams can both travel through a same, single microlens array, the degree of precision is reduced making the system easier and cheaper to fabricate.

In one example, the system may utilize a collimated laser beam to illuminate an array of microlenses (as an example 460 mm diameter, 6-12 mm focal length) etched on a fused-silica disk. The microlenses can be arranged in a hexagonal pattern such that the illuminating beam is split into small beams, which may be referred to as beamlets, and focused into an array of foci of ~6 mm beam waist at the prefocusing plane (PFP). After the intermediate optics, the beamlets are directed into a conventional fluorescence microscope including at least the objective shown in FIG. 1. The role of the intermediate optics is to ensure that the array of foci is imaged into the focal plane of the objective and that each beamlet is parallel at, and over-illuminates, the objective entrance pupil. The objective lens 175 then produces a pattern of high-resolution foci at the sample.

The microlenses 120 can be arranged with a constant helical pitch, forming spirals, such as with 10 rows, in a Nipkow style disk. The layout and, in particular, the spiral pitch of the microlenses 120 can be designed in such a way that the disk 130 contains several (typically 3-12) equivalent segments. The layout of the microlenses 120 is selected such that upon rotation, each segment produces a complete scan of the focal area. Upon rotation of the disk 130, each microlens 120 scans one line in the sample. The distance between the lines of two subsequent microlens foci in the sample remains well below the lateral resolution, assuring homogeneous scanning of the sample. The round microlenses can be hexagonally closed-packed.

Rotating the microlens disk 130 by 360° renders as many complete lateral scans as segments on the disk 130, typically 5 to 12. The disk 130 can be rotated at more than 100 Hz resulting in scanning rates of more than 1000 frames/s. Unlike galvanometer-based scanners, this scanning mechanism does not involve any dead time. The image rate is ultimately determined by the camera frame rate, depending on the readout rate and the number of pixels. It may range well above 30 images/s. The signal is readily separated from the excitation light by a dichroic mirror and imaged directly onto a EMCCD (Electron Multiplying Charge Coupled Device) or sCMOS (scientific or scalable Complementary Metal Oxide Silicon) camera (i.e., imaging device 100). With faster and more sensitive cameras, the actual limit can be determined by the number of multi-photon-induced signal photons that are produced in the focal plane. Blocking near-infrared (NIR) excitation light in the eyepieces with an absorption filter allows real-time observation of multi-photon generated images by eye.

The introduction of the electron multiplying charge coupled device (EMCCD) revolutionized the field of single molecule detection with its unprecedented optical sensitivity by using a separate amplification step based on impact ionization. However, no EMCCD with >1.2 megapixel format is commercially available, thus inherently limiting the available FOV. If an imaging setup requires multiple simultaneous channels (e.g. spectral channels for multi-color applications, focal channels for multi-focal plane approaches) imaged on one chip, the FOV is reduced even further. In addition, EMCCDs can only be read out at moderate frame rates, typically 30-75 frames/s for a full FOV. Faster frame rates are only achievable by reducing the total number of pixels (and thus FOV). For instance, up to 900 Hz image acquisition rate has been recently reported by limiting the FOV to only 64×128 pixels (35). Separately, EMCCDs also suffer from a unique noise source due to the multiplication gain register, adding an additional noise factor that effectively halves the nominal quantum efficiency (QE) of EMCCDs, and thus their overall sensitivity (38).

Recent advances in complementary metal oxide semiconductor (CMOS) based imaging detectors have begun to challenge the primacy of EMCCD use in many microscopy applications. These "scientific grade" CMOS (sCMOS) detectors offer much larger pixel arrays, up to five megapixels, with relatively low readout noise (1-2 e$^-$) and without the multiplication noise of EMCCDs. Further, due to more flexible readout architecture, overall image acquisition speed is significantly higher than EMCCDs (e.g. one hundred 4-megapixel frames/s).

The present technology includes improvements which incorporate the latest generation sCMOS cameras or detectors from all major vendors. Such detectors may allow multiple (up to 8) simultaneous image channels, each comprised of 200×400 pixels, to be read out at 1000 frames/sec (fps), with further FOV (field of view) reductions enabling up to 3000 fps. This represents an order of magnitude increase in FOV with four times the number of imaging channels, while maintaining higher overall raw data acquisition rates compared to that reported previously. Careful optical design is necessary to avoid artifacts. Specifically, sCMOS readout mechanisms can result in each horizontal pixel line being exposed and digitized at slightly different time points. Multiple simultaneous channel acquisition will suffer inaccuracies unless corresponding features in each channel occupy identical rows in the pixel array. As such, the present technology may utilize a multi-color optical design that results in up to eight image channels arranged in a linear array (i.e., 1×4 grid) on a rectangular sCMOS detector (in contrast to other layouts where the four channels may be arranged in a grid or other pattern, such as a 2×2 grid layout to be detected on a square sCMOS detector). Use of a rectangle image sensor or use of a portion of an image sensor, rectangular or otherwise, may reduce processing times such as when the portion of image sensor used is less than the full image sensor because there is less data to process.

The pinholes 140 allow light only from a focal surface of the sample to pass through. The pinholes 140 can have a diameter of approximately 10-50 μm, for example, although other diameters may also be used. There can be a predetermined distance between the microlens disk 130 and the pinhole disk 150. When the motor provides rotation force to a coupling drum 135, the microlens disk 130 and the pinhole disk 150 can integrally rotate. A motor control unit can control the motor. The motor control unit can cause the motor to rotate to apply rotation force to the coupling drum. The microlens 130 and pinhole disks 150 can be coupled to the coupling drum 135.

The microlens array 125 may include one lens/pitch size. The focal length of the microlens array can be designed to work with the optical construction of the system and the numerical aperture of the objective. However, the microlens array 125 can be fabricated with separate regions of lens size/pitch/focal length. Smaller lens/pitch size result in faster imaging but higher cross talk between different foci. Larger lens/pitch size will reduce the cross talk and can be useful for imaging thick samples but will also result in slower imaging times. Additionally, the pinhole size can be different for different regions of the array. Smaller pinholes increase sectioning ability but reduce throughput. Larger pinhole decrease sectioning but result in higher throughput. The pinhole array can have regions with different pinhole sizes. The desired pinhole region can be inserted accurately into the optical path by using a piezo actuator. The microlens array and the pinhole array can have regions with different lens (pitch) size. By having microlens and pinhole arrays with different size or pitch options, the user can decide what tradeoff works best for a specific sample.

A Nipkow microlens disk 130 can be a disk with spiral pattern of holes arranged to raster scan the sample with the excitation light and impinge on the sample with numerous small points of light to enable scanning the sample when the microlens disk is spinning. As will be appreciated by one of skill in the art, a Nipkow disk may include any number of design configurations or arrangements which may differ from or by more sophisticated than the original Nipkow disk. Such configurations and arrangements are contemplated and are considered to be a part of this disclosure. The microlens disk 130 can include thousands or tens of thousands of microlenses. Each microlens 120 can focus the emission beam 112 onto the corresponding pinhole 140. Using the microlens disk 130 in the excitation beam path increases laser intensity in comparison to a standard pinhole arrangement without microlenses. Up to 1,000 or more excitation beams can fill the aperture of the objective lens 175, and are then focused on the focal plane. Fluorescence generated from the sample is captured by the objective lens and focused back through the microlens array 125 and optionally onto the pinhole disk 150, then transmitted through the holes to eliminate out-of-focus signals and be focused into the image plane in the eyepiece or camera (e.g., image detector 100).

In one example, a distance between the microlenses 120 can be approximately 100 microns, or 100 nm. The disk 130 may scan 1,000 lines to scan the sample, using 100 foci. The microlens disk 130 can rotate at 7,200 RPM=120 rotations per seconds=120 triple-scans per second=360 single scans per second, where one full rotation of the microlens disk 130 corresponds to three scans. In another example, rotation of the microlens disk 130 at 15,000 RPM results in ~750 single scans/second. By rearranging the microlenses 120 on the microlens disk 130 such that ¼ rotation is a full scan, 15,000 RPM would result in 1,000 single scans/second.

A plurality of lasers (e.g., light source 105), such as 405 nm, 488 nm, 561 nm, and 647 nm can be used as light sources. Other wavelengths, numbers of light sources, and types of light sources can also be used. Although specific light sources may be mentioned herein, other types of light sources can also be used to provide the functions of activation and readout as described herein. The 405 nm laser or other lasers can be used to activate a set or a subset of probe molecules. A selected range of intensities can be used to convert only a sparse subset of molecules at a time, e.g. to activate at least one molecule with at least one activation photon. Although powers can vary, a power ranging from about 0.01 μW to 1.0 mW can be suitable in some cases. The power used can depend on the particular probe molecules and sample characteristics. Generally, a minimum of 25 mW may be considered. Lower powers can be used, which may reduce the number of photons acquire for the image acquisition. Use of a very high powered 561 nm laser, e.g. 200 mW, for example, can result in a more rapid process of excitation, collection and bleaching than may result from a lower powered laser or light source, at the risk of not being able to image the sample for an extended amount of time.

Although other probe molecules may be suitable, the probe molecules used herein can generally be fluorophores or organic dyes for fixed specimens. The fluorophores can be imaged either sequentially or simultaneously. In one optional aspect, the cells can include at least two or more species of flourophores to allow simultaneous or subsequent imaging of at least two different subsets of materials. The fluorophores may be configured to use Forster resonance energy transfer (FRET) to transfer energy to another probe molecule or to accept energy from another molecule. Broadly, the fluorophores can be an energy transfer donor or an energy transfer acceptor.

While some of the dyes discussed herein may be photoactivatable fluorophores, meaning they are first activated and then excited, it is to be understood that non-photoactivatable dyes which are driven into a dark state and then imaged when they reappear from the dark state can also be used. Single step dyes or probes may also be used. For example, a single step dye may be used which is activated/excited and bleached in one step. While dyes discussed herein have included red and green colors, it is to be understood that dyes can be in many different colors. A suitable laser or light source at a corresponding wavelength may be used to activate and/or excite the colors being used.

An acoustic optical tunable filter (AOTF), controllable through software provides the ability to properly attenuate multiple light sources simultaneously and control the efficiency of activation, excitation and bleaching. For example, a 488 nm laser line allows one to image or locate photoactivatable fluorescence proteins prior to conversion by the 405 nm laser, from a visibly green fluorescence to red fluorescence.

The AOTF can provide external control of light source intensity for modulating the light beam. The AOTF can also be used to control the direction or position of the light beam. For example, where the microlens array includes lenses of differing sizes or pitches, the AOTF can direct the excitation beam to the appropriate region of the microlens disk. Software can be used to control the AOTF to vary illumination intensity, direction or position of the light sources independently of any other filters. The AOTF can be configured to control the light sources to provide time-dependent sequences of illumination of at least one wavelength. An optical fiber can connect the light source to the AOTF. An optical fiber combiner can combine the optical power carried by two optical fibers, such as from a plurality of light sources into a single output fiber.

The imaging device 100 can be a CCD camera, which can optionally be an electron multiplying charge coupled device (EMCCD). In one alternative aspect, the camera system can comprise a plurality of cameras. An optional external liquid cooler can be used to cool the EMCCD. The liquid cooler can use thermoelectric cooling to cool the EMCCD. The EMCCD can include one or more detection channels. The camera can capture images of one or more molecules at a single instant or as a function of time. The system can include a particle analysis module in communication with the camera and configured to provide analysis of particle tracking. Photoactivatable dyes within a sample can be activated with UV activation.

The system can include a plurality of mirrors 160, 190 to direct a light beam along the light path as illustrated. The various optics, apertures, beam splitters, and so forth used in the system can be installed on a construction rail, microdovetail rail, or the like. The system can be set up on a table or other surface, and may also include a computer having a memory and a processor configured to process data and operate the software.

A widefield microscope stand can be used to support the sample, although other stands can be suitable. An isolation table can be used to reduce vibration of the system and prevent undesirable artifacts from being introduced into the collected data.

Figure 2:
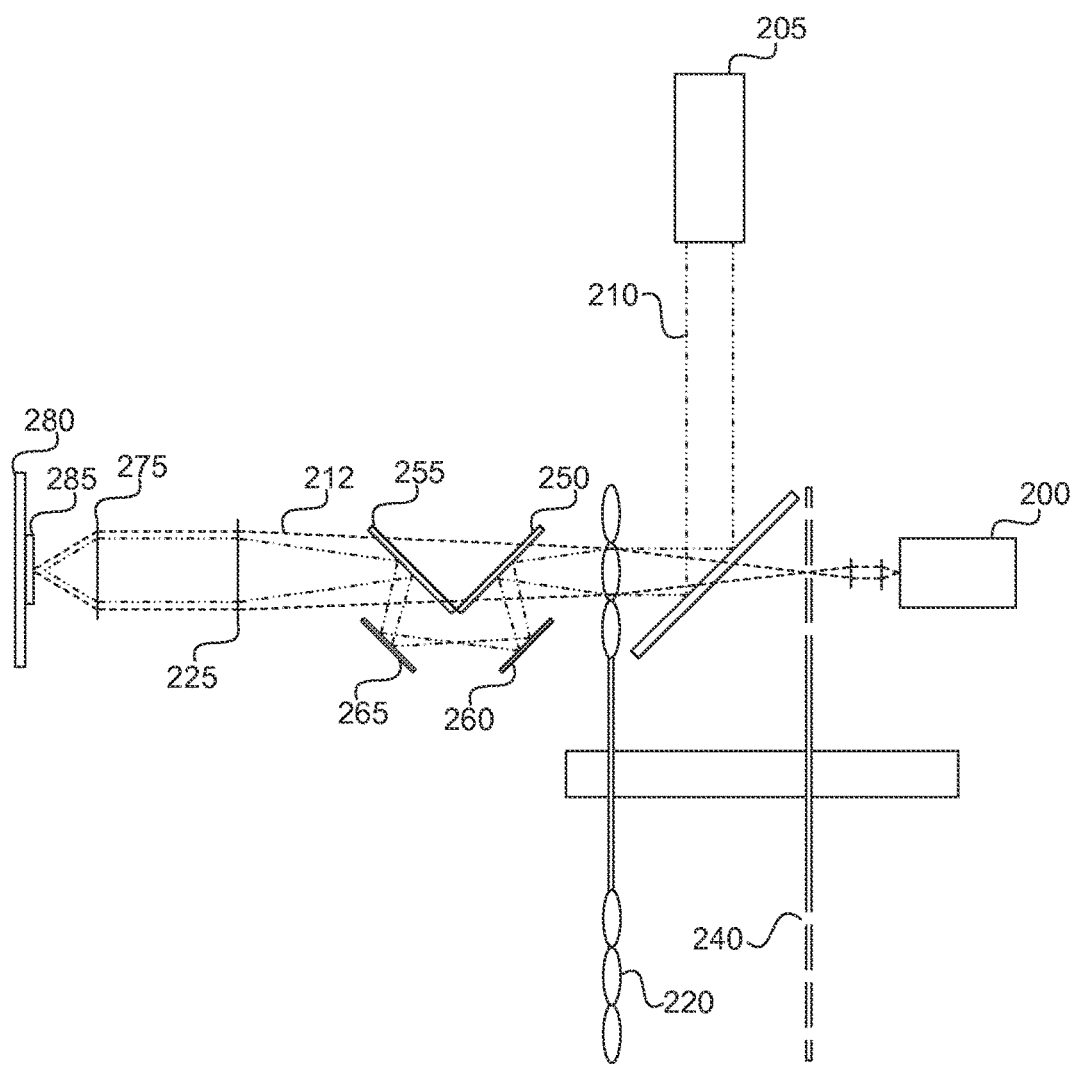

FIG. 2 illustrates another example microscope system configured to decouple the excitation 210 and emission beam paths 212. In this example, the distance the excitation light 210 travels between the microlenses 220 and tube lens 225 is longer than the emission path 212 length. Therefore, the excitation can travel a total distance of $d_{ex}=f_{TL}+f_{ML}$ between the microlenses 220 and tube lens 225 while the emission travels a total distance of $d_{em}=f_{TL}-f_{ML}$, consistent with the example illustrated in FIG. 1. In this example, the excitation beam 210 path length is longer by being redirected by dichroic mirrors 250, 255 and mirrors 260, 265, while the emission beam 212 passes through the dichroic mirrors 250, 255.

The coherent light of the excitation beam 210 can be expanded to yield the desired beam size. The beam 210 passes through the microlenses 220 which creates multi-foci excitation. The multi foci excitation beam is projected onto a fluorescence sample 285 on the sample stage 280 by a microscope objective 275. The fluorescence emission is collected by the microscope objective 275 and directed back through the microlenses 220 toward the image detector, by which super resolution is achieved. If placed in the correct place, the microlenses 220 will modify the local magnification (the exact magnification factor depends on the exact position of the microlens array). Pinholes 240 can be placed in the imaging plane in order to regain sectioning ability. The imaging device 200 can collect the light, such as for one full scan. The resulting image will have improved resolution as compared with conventional technologies. Post analysis of the images can further improve the resolution by up to a factor of root 2.

Figure 3:
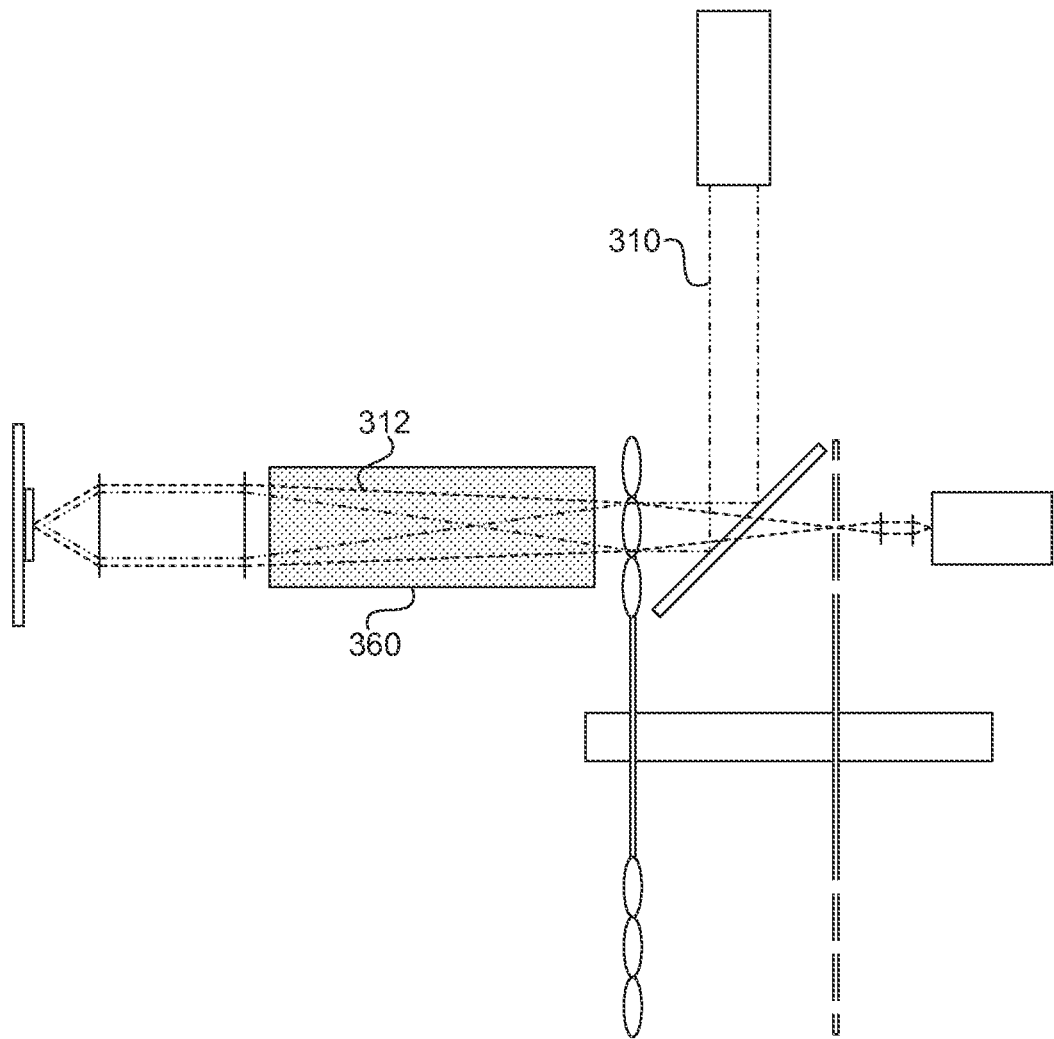
FIG. 3 is a schematic view of a super resolution microscopy system including a material having a different refractive index for the excitation and emission beams in accordance with an example of the present technology.

FIG. 3 illustrates another example microscope system. In this example, the optical path length of the emission 312 and excitation beams 310 can be different by directing the beams 310, 312 through a material 360 with specific properties. The optical path difference between the excitation wavelength and emission wavelength may satisfy the following condition:

$$\Delta OPL = (n_1 - n_2)d = 2f_{ML}$$

where n1 is the refractive index of the excitation beam, n2 is the refractive index of the emission beam and d is the distance the light travels though the material 360. In this example, the material 360 can have a different refractive index for the excitation 310 and emission beams 312 such that the speed of the transmission through the material 360 differs and effectively results in a longer path length for the excitation beam 310.

This technology can be combined easily with multi-color excitation and detection or with polarization dependent imaging. One way to achieve multi-color imaging is by splitting the detection path into two image detectors using a dichroic mirror in the emission path as illustrated above. In this case, each image detector will detect a different color. The same works for different polarization by simply switching the dichroic mirror with a polarization beam splitter. Another way to accomplish multi-color imaging is to split the signal onto two separate the regions on the camera, where each region records a different color or polarization.

Instantaneous multi-color imaging with super resolution will enable biologists to study multiple probes at the same time. This is even more important for live or dynamic samples where instantaneous imaging of two or more colors becomes more important.

The present super resolution microscopy system can be combined with two-photon microscopy in order to yield super resolution two-photon images. The advantage of two-photons is its sections capabilities. Therefore, the pinhole array in this case can be removed. The present super resolution microscopy system can also be combined with single molecule localization microscopy. Typically in single molecule localization the sample is imaged with widefield microscopy and the molecules are localized in the post analysis. The widefield imaging can be replaced by the super resolution technique described in this patent. The improved resolution of the images will result in better localization accuracy.

Figure 4A:
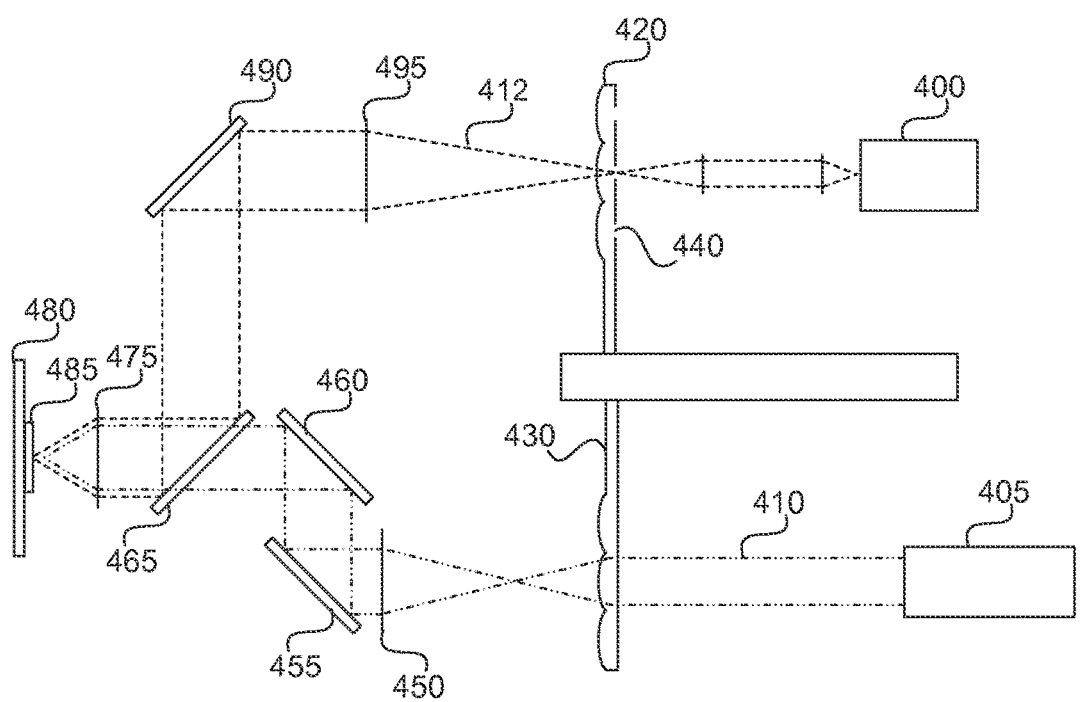
FIG. 4A is a schematic view of a super resolution microscopy system including a microlens disk having a pinhole array on one half of one side of the microlens disk in accordance with an example of the present technology.
Figure 4B:
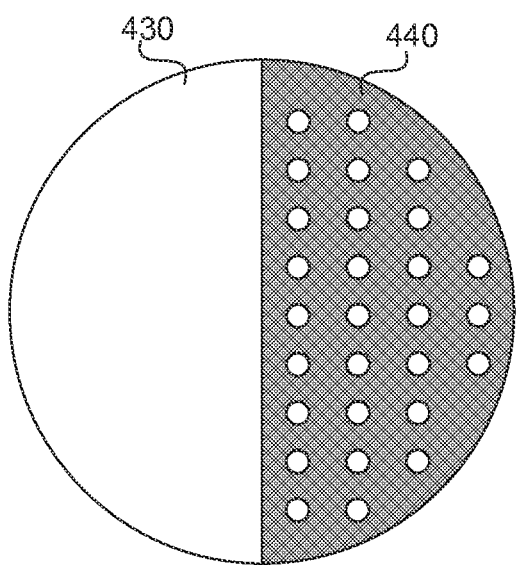
FIG. 4B is a simplified front view of the microlens disk of FIG. 4A.

Reference will now be made to FIGS. 4A-4B. FIG. 4A illustrates a super resolution microscopy system in accordance with an example which results in super resolution images. In this example, a single disk 430 having both a microlens array 420 and a pinhole array 440 is provided. However, the pinhole array 440 is provided only on half of the disk 430, as illustrated in FIG. 4B. The half of the disk 430 including the pinhole array 440 can be opaque where the pinholes are not present and the half of the disk not including the pinholes can be transparent or translucent. The pinhole array 440 shown in FIG. 4B can be arranged in any other suitable pattern, such as helical or the like. The halves of the disk 430 can be arranged symmetrically without being divided in half along a straight line across the middle. Alternatively, the pinhole and non-pinhole portions of the disk may be arranged asymmetrically and in a different size ratio than 1:1.

The excitation beam 410 passes through one side of the disk 430 while the emission beam 412 passes through the other side of the disk 430. Specifically, the excitation beam 410 passes through the half of the disk 430 lacking the pinholes while the emission beam 412 passes through the half of the disk 430 possessing the pinholes. This arrangement essentially decouples the two paths and enables putting tube lenses 450, 495 at different distances from the microlens array 420. The distance specifications are similar to the examples described with respect to FIGS. 1-3. The laser light source 405 can be synchronized with the spinning disk 430 in such a way that the light source 405 is switched on when aligned with the part of the disk 430 without the pinholes. Therefore, the illumination will pass through the microlens array 420 without going through the pinhole array 440 while the emission beam 412 will go through the microlens array 420 and be focused on the pinhole array 440. The light source 405 can be switched off when aligned with the part of the disk 430 with the pinhole array 440.

The pinhole array 440 can either be constructed on a separate disk (as in the previous examples) or coated on the back of the microlens array 420 (as illustrated). When the pinhole array 440 is coated on the back of the microlens array 420, the microlens array 420 thickness can be adjusted such that an imaging plane is formed on the pinhole mask. In one example, the system may omit the pinhole array 440.

The configuration of FIG. 4A reduces the amount of disks to either two disks or even one disk. This greatly reduces the complexity of the setup. Another advantage of this design is that there is no need for a dichroic mirror to be placed between the two disks. In order to fit a dichroic between the two disks, compromises in certain parameters such as the microlenses size, field of view and microscope objective numerical aperture may be made. Without the dichroic, these parameters can be chosen based on imaging needs (instead of geometry constraints).

The microlens array and pinhole array can be manufactured as one unit or can be combined into one unit. When combining the arrays 420, 440, the two arrays 420, 440 can be aligned with respect to each other and then glued together. Another example implementation is to put a pinhole mask on the back of the microlens array 420. In this example, the microlens thickness can be designed in such way that an image plane will be formed exactly at the edge of the flat part.

Conventionally, the microlens array 420 and pinhole array 440 are on different mounts and are aligned with respect to each other. However, the alignment is a complicated process. Furthermore, the mounts can drift over time, requiring time consuming readjustment which is difficult to automate. Combining the two arrays 420, 440 together reduces the need to have two independent and adjustable mounts and results in arrays which do not drift over time with respect to one another. Also, because this single unit uses only a single mount (instead of two or more), the combined disk makes more space available in typically compact designs.

Figure 5:
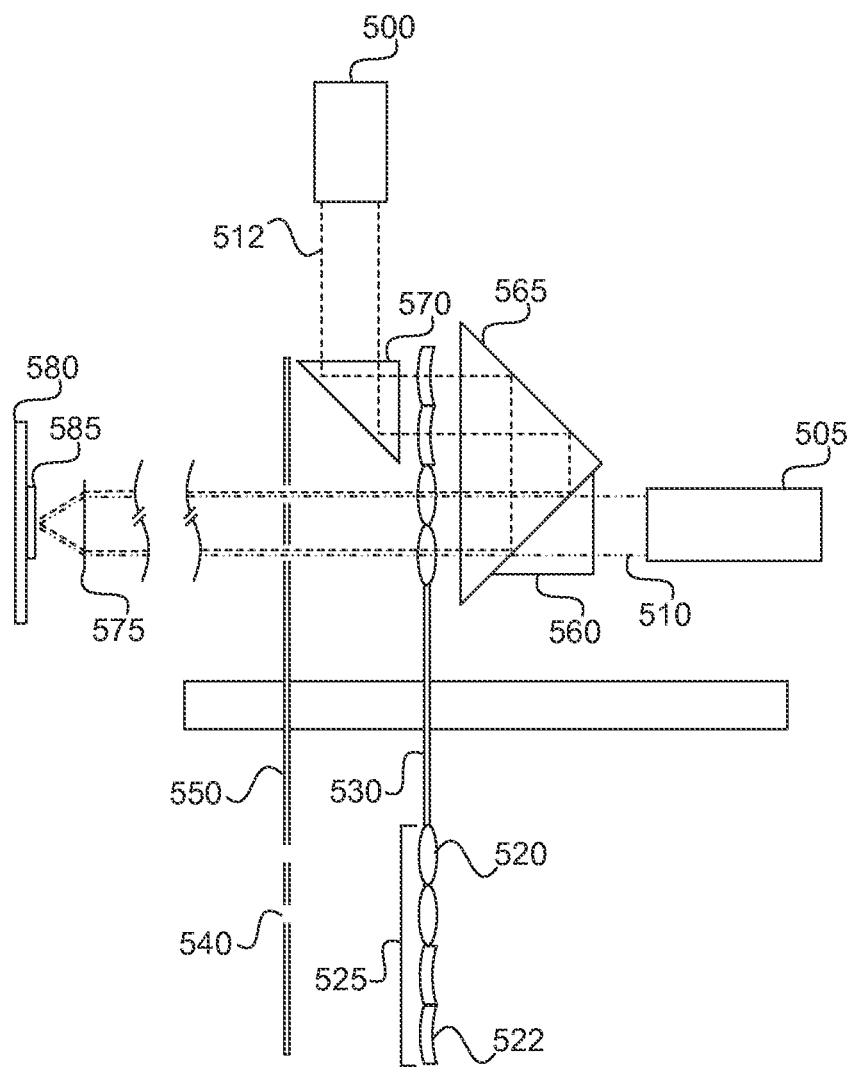
FIG. 5 is a schematic view of a super resolution microscopy system including a microlens disk having concave and convex lens arrays at differing radii in accordance with an example of the present technology.

FIG. 5 illustrates another example implementation. In this example, multiple different types of lenses 520, 522 are included on the microlens disk 530. For example, rather than using multiple microlens disks including positive and negative lenses, or converging and diverging lenses, a single disk 530 comprises converging and diverging lenses 520, 522. An additional disk 550 including pinholes 540 can be optional. The excitation light 510 can be transmitted through a plurality of adjacent prisms 560, 565, through converging lenses 520 of the microlens array 525, and through pinholes 540, if present, toward the sample 585 on the sample stage 580, being focused by an objective lens 575. The emission light 512 will pass through the pinhole disk 550, through the converging lenses 520 on the microlens disk 530, be redirected in prism 565 back toward the microlens disk 530 to pass through the diverging microlenses 522, and then be redirected toward the image detector 500 using a prism 570, mirror or the like. Prism 565 can pass the excitation beam 510 but deflect the emission beam 512 by including a dichroic coating between prism 565 and 560. The converging lenses may be positive lenses and the diverging lenses may be negative lenses. Placement of the negative lens and relationship of the focal lengths of the positive and negative lenses can be selected such that the negative microlenses have half the focal length of the positive microlenses. The distance the luminescence travels between passing through the positive and negative microlenses (e.g., the distance the emission beam passes through prism 565) can be the difference of the focal lengths. The positive and negative microlenses can form a Galilean-type telescope with magnification of ½. Use of this combination of microlenses in the path of demagnified images (e.g., the luminescence) and spinning the microlens disks synchronously with camera exposure can result in pinholing, scaling, and summing the luminescence to achieve a resolution doubling (e.g., super resolution). In some cases, resolution can be improved to about 140 nm.

Figure 6:
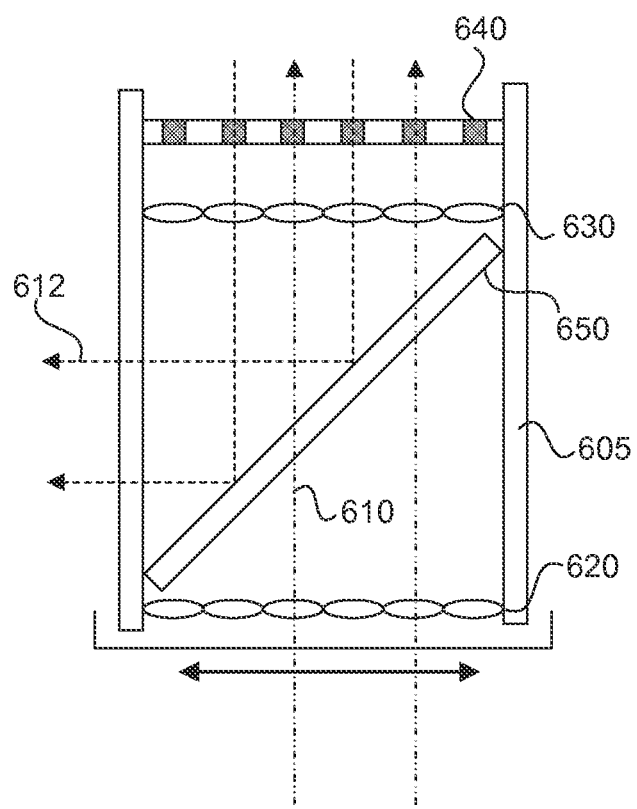
FIG. 6 is a schematic view of a super resolution microscopy system including microlens arrays and a pinhole array in a non-rotating, scanning configuration in accordance with an example of the present technology.

While the foregoing examples primarily refer to spinning disk configurations, FIG. 6 illustrates an example non-spinning disk configuration. Specifically, a plurality of arrays 620, 630, 640 and a dichroic mirror 650 are held together in a frame 605. The arrays can include one or two microlens arrays 620, 630 and an optional pinhole array 640. As with the previous examples, the excitation beam 610 and emission beam 612 can both pass through a same microlens array 630. Rather than rotating the arrays 620, 630, 640, the frame 605 securing the arrays 620, 630, 640 can be moved, such as by shaking, vibrating, etc. in two or more directions vertically and/or laterally. The three arrays 620, 630, 640 can be mounted at the appropriate distances from one another other and moved. The array 620 may have diverging lenses depending upon the configuration. The placement of the arrays 620 and 630 will allow for optimal resolution when coordinated with the rest of the optical path. The motion will allow the scanning of the light in the sample (similar to a spinning disk). A shaking or other motion can be created, for example, by coupling the frame 605 to a motor, to a piezo actuator, to scanning galvos, etc. The frame 605 can be moved in a raster pattern, for example. To couple the arrays 620, 630, 640 in the frame 605, the arrays 620, 630, 640 can first be aligned optically to each other and then glued together.

Furthermore, the system may also be combined with multi-color excitation and detection or with polarization dependent imaging. For example, multi-color imaging may be achieved by splitting a detection path (e.g., the emission path) toward two cameras. This may be accomplished using a dichroic mirror, for example. In this case, each capturing device may detect a different color. The same principle can be applied to different polarization by simply switching the dichroic mirror with a polarization beam splitter. In an alternative embodiment, multi-color imaging may be realized by splitting the multi-foci emission light onto two separate the regions on a capturing device, where each region records a different color and/or polarization.

In this or other examples, a feedback module can be used to provide user feedback triggering image acquisition using an analog voltage representing the total fluorescence output of the camera. An analog circuit can be used to generate a TTL logic pulse when the voltage is within a predetermined range. An integrated circuit or voltage comparator can apply the TTL voltage back to the camera to gate image acquisition.

In one aspect, the system can include a multi-well plate imaging module configured to automatically move from one sample well to another to image a plurality of sample wells. The multi-well plate imaging module can be configured to automatically translate the sample in any direction to provide optimal imaging. Also, the multi-well plate imaging module can be configured to simultaneously image any number of individual molecules within a single cellular compartment.

Molecule-molecule binding of molecules in the sample can be measured using a molecule-molecule binding measurement module. The sample can optionally include living cells. In some situations, it may be useful to image these cells in various environments and in differing conditions. The system described herein may be used for samples which are in vivo, ex vivo, in vitro, perfused, etc. In one alternative aspect, the sample may be incubated in gas. In the case of a gas-incubated sample, the system can further comprise a gas control module configured to control the gas in which the sample is incubated. To better control the sample environment, the system can include a temperature control module configured to control a temperature of the sample and/or a humidity control module configured to control a humidity of the sample.

The system can include multiple microscope types for simultaneous or sequential imaging of the sample. This could include examples such as multipoint confocal (as discussed), single molecule localization super resolution, light-sheet, and laser scanning confocal microscopy or Confocal with STED. Alternately, or additionally, the system can include an electron microscope configured to acquire electron microscope images of the sample simultaneously or sequentially with the camera. Some examples of contemplated electron microscopes include a scanning electron microscope (SEM) and a transmission electron microscope (TEM).

The molecular understanding of disease has become of increasing interest in the era of "personalized medicine," including accurate identification of diagnostic/prognostic biomarkers, as well as development of corresponding targeted therapeutics and response monitoring protocols. Treatment of diseases such as breast cancer, atherosclerosis, and Alzheimer's disease has been greatly impacted by the identification of proteomic and genomic signatures. Optical microscopy remains a primary approach for elucidating spatiotemporal behavior of disease-associated biomolecules. The introduction of super resolution microscopy has eroded this mismatch, allowing optical imaging to enter the nanoscale regime. In the past several years, a number of researchers have reported unique biological insights with the aid of super resolution microscopy. These include studies of DNA/chromatin structure, fundamental neuronal behavior, cardiovascular applications, and infectious disease mechanisms. While it is expected that "nanoscopy" will become increasingly useful in aiding researchers to formulate new understanding, significant improvements in current commercial technology are sought to increase the utility, flexibility, and resolving power of super resolution microscopy.

While certain aspects of the present technology have been described in terms of use in fluorescent microscopy, the application of the present technology may not be limited to any particular field of study. For example, the present technology may be used in medical diagnostics or other industries as well. Specifically in such an application, and by way of non-limiting example, the probe molecules as described herein may correspond to molecules used to tag blood samples or the like. Some specific, non-limiting example molecules may include class I and class II molecules that are leczymes in humans and encoded by genes within the HLA-D region such as HLA-DP, HLA-DN, HLA-DM, HLA-DO, HLA-DQ or HLA-DR, or the various alleles of HLA-A, HLA-B and HLA-C loci, or the HLA-X, HLA-E, HLA-J, HLA-H, HLA-G and HLA-F genes.

Figure 7:
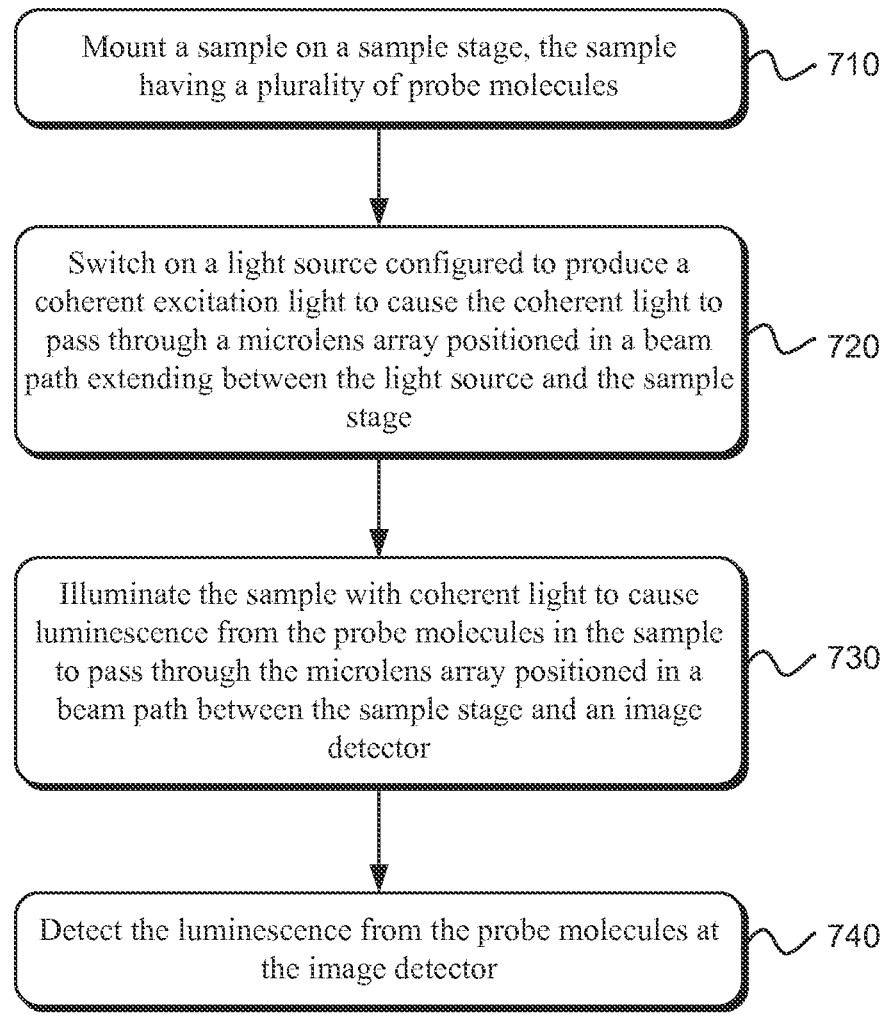
FIG. 7 is a flow diagram of a method for performing super resolution microscopy in accordance with an example of the present technology.

FIG. 7 illustrates a flow diagram of a method according to the present technology. For simplicity of explanation, the method is depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events. Additionally, it should be appreciated that at least a portion of methods disclosed in this specification are capable of being stored on an article of manufacture to facilitate transporting and transferring such methods to computing devices. The term article of manufacture, as used herein, is intended to encompass a computer program accessible from any computer-readable device or storage media.

Any of a variety of other process implementations which would occur to one of ordinary skill in the art, including but not limited to variations or modifications to the process implementations described herein, are also considered to be within the scope of this disclosure.

In one example, a method for performing super resolution microscopy is provided. The method includes mounting 710 a sample on a sample stage, the sample having a plurality of probe molecules. The method further includes switching 720 on a light source configured to produce a coherent excitation light to cause the coherent light to pass through a microlens array positioned in an excitation or coherent beam path extending between the light source and the sample stage. The sample is illuminated 730 with coherent light to cause luminescence from the probe molecules in the sample to pass through the microlens array positioned in an emission or luminescence beam path between the sample stage and an image detector. The method can include rotating the microlens array while illuminating the sample. The luminescence from the probe molecules can be detected 740 at the image detector.

In a more detailed example, the method includes rotating a pinhole array oriented in the beam path between the sample stage and the image detector in synchronization with rotating the microlens array.

In a more detailed example, the microlens array is arranged in a circular pattern and the pinhole array is arranged in a semi-circular pattern. The method further includes switching the light source off when the pinhole array is rotated in the beam path between the light source and the sample stage and switching the light source on when the pinhole array is rotated out of the beam path between the light source and the sample stage.

In some examples, this or other methods described herein may be implemented wholly or partially as computer readable program code executed by a processor and the computer readable code may be embodied on a non-transitory computer usable medium.

Figure 8:
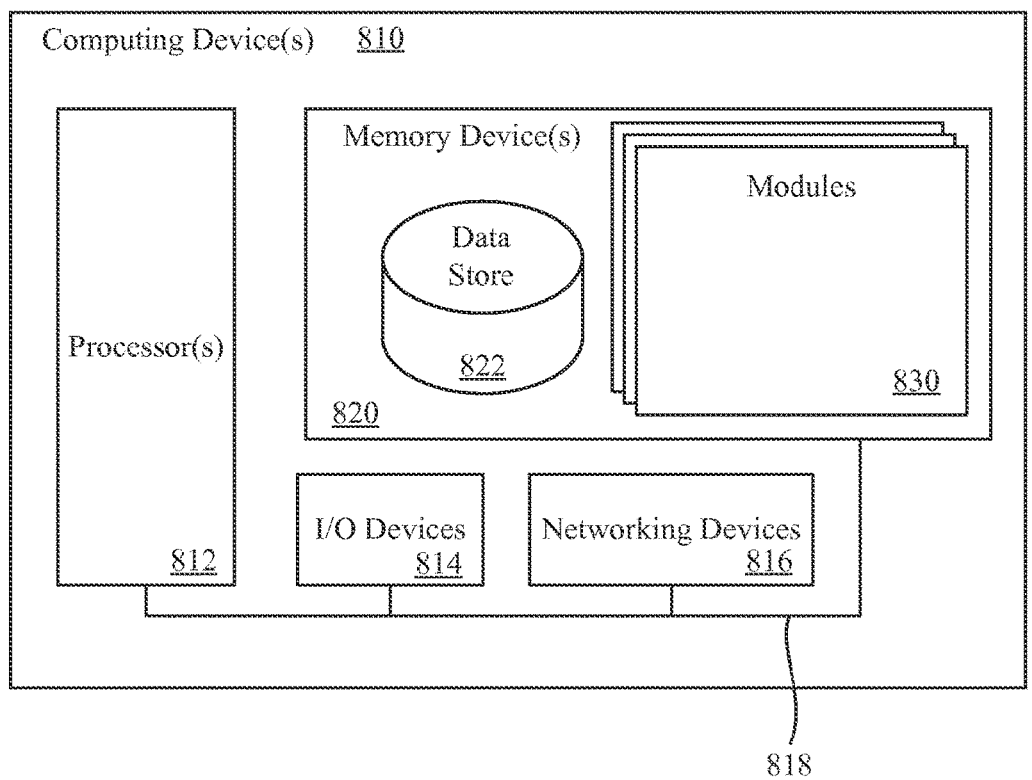
FIG. 8 is a schematic diagram of a computing system for use in performing portions of the super resolution microscopy methods in accordance with an example of the present technology.

FIG. 8 illustrates a computing device 810 on which services or modules of this technology may execute. A computing device 810 is illustrated on which a high level example of the technology may be executed. The computing device 810 may include one or more processors 812 that are in communication with memory devices 820. The computing device 810 may include a local communication interface 818 for the components in the computing device. For example, the local communication interface 818 may be a local data bus and/or any related address or control busses as may be desired.

The memory device 820 may contain modules 830 that are executable by the processor(s) and data for the modules. A data store 822 may also be located in the memory device 820 for storing data related to the modules and other applications along with an operating system that is executable by the processor(s) 812.

The computing device 810 may further include or be in communication with a client device, which may include a display device. The client device may be available for an administrator to use in interfacing with the computing device 810, such as to review operation of a virtual computing instance, make improvements to machine learning models and so forth.

Various applications may be stored in the memory device 820 and may be executable by the processor(s) 812. Components or modules discussed in this description that may be implemented in the form of software using high programming level languages that are compiled, interpreted or executed using a hybrid of the methods.

The computing device 810 may also have access to I/O (input/output) devices 814 that are usable by the computing devices. An example of an I/O device 814 is a display screen that is available to display output from the computing devices. Other known I/O device may be used with the computing device as desired. Networking devices 816 and similar communication devices may be included in the computing device 810. The networking devices 816 may be wired or wireless networking devices 816 that connect to the internet, a LAN, WAN, or other computing network.

The components or modules that are shown as being stored in the memory device 820 may be executed by the processor 812. The term "executable" may mean a program file that is in a form that may be executed by a processor 812. For example, a program in a higher level language may be compiled into machine code in a format that may be loaded into a random access portion of the memory device 820 and executed by the processor 812, or source code may be loaded by another executable program and interpreted to generate instructions in a random access portion of the memory to be executed by a processor 812. The executable program may be stored in any portion or component of the memory device 820. For example, the memory device 820 may be random access memory (RAM), read only memory (ROM), flash memory, a solid state drive, memory card, a hard drive, optical disk, floppy disk, magnetic tape, or any other memory components.

The processor 812 may represent multiple processors and the memory 820 may represent multiple memory units that operate in parallel to the processing circuits. This may provide parallel processing channels for the processes and data in the system. The local interface may be used as a network to facilitate communication between any of the multiple processors and multiple memories. The local interface may use additional systems designed for coordinating communication such as load balancing, bulk data transfer, and similar systems.

While the flowcharts presented for this technology may imply a specific order of execution, the order of execution may differ from what is illustrated. For example, the order of two more blocks may be rearranged relative to the order shown. Further, two or more blocks shown in succession may be executed in parallel or with partial parallelization. In some configurations, one or more blocks shown in the flow chart may be omitted or skipped. Any number of counters, state variables, warning semaphores, or messages might be added to the logical flow for purposes of enhanced utility, accounting, performance, measurement, troubleshooting or for similar reasons.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices. The modules may be passive or active, including agents operable to perform desired functions.

The technology described here may also be stored on a computer readable storage medium that includes volatile and non-volatile, removable and non-removable media implemented with any technology for the storage of information such as computer readable instructions, data structures, program modules, or other data. Computer readable storage media include, but is not limited to, RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which may be used to store the desired information and described technology. The computer readable storage medium may, for example, be in the form of a non-transitory computer readable storage medium. As used herein, the terms "medium" and "media" may be interchangeable with no intended distinction of singular or plural application unless otherwise explicitly stated. Thus, the terms "medium" and "media" may each connote singular and plural application.

The devices described herein may also contain communication connections or networking apparatus and networking connections that allow the devices to communicate with other devices. Communication connections are an example of communication media. Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared, and other wireless media. The term computer readable media as used herein includes communication media.

It is noted that any of the distributed system implementations described above, or any of their components, may be implemented as one or more web services. In some implementations, a web service may be implemented by a software and/or hardware system designed to support interoperable machine-to-machine interaction over a network. A web service may have an interface described in a machine-processable format, such as the Web Services Description Language (WSDL). Other systems may interact with the web service in a manner prescribed by the description of the web service's interface. For example, the web service may define various operations that other systems may invoke, and may define a particular application programming interface (API) to which other systems may be expected to conform when requesting the various operations.

In various implementations, a web service may be requested or invoked through the use of a message that includes parameters and/or data associated with the web services request. Such a message may be formatted according to a particular markup language such as Extensible Markup Language (XML), and/or may be encapsulated using a protocol such as Simple Object Access Protocol (SOAP). To perform a web services request, a web services client may assemble a message including the request and convey the message to an addressable endpoint (e.g., a Uniform Resource Locator (URL)) corresponding to the web service, using an Internet-based application layer transfer protocol such as Hypertext Transfer Protocol (HTTP).

In some implementations, web services may be implemented using Representational State Transfer ("RESTful") techniques rather than message-based techniques. For example, a web service implemented according to a RESTful technique may be invoked through parameters included within an HTTP method such as PUT, GET, or DELETE, rather than encapsulated within a SOAP message.

Reference was made to the examples illustrated in the drawings, and specific language was used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure, are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology may be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements may be devised without departing from the spirit and scope of the described technology.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A super resolution microscope system, comprising:
a sample stage adapted to receive a sample;
at least one light source configured to produce a coherent excitation light and cause luminescence of probe molecules in the sample;
an image detector configured to detect the luminescence from the probe molecules; and
a microlens array positioned in a beam path of the coherent light from the at least one light source, the beam path of the coherent light extending between the at least one light source and the sample stage, the microlens array being also positioned in a beam path of the luminescence from the probe molecules, the beam path of the luminescence extending between the sample stage and the image detector
wherein one or both of:
the microlens array comprises a plurality of converging lenses and a plurality of diverging lenses, the microlens array being positioned to transmit the coherent light through the plurality of converging lenses and to transmit the luminescence through the plurality of diverging lenses; and
the system further comprises a pinhole array oriented in at least one of the beam path of the coherent light and the beam path of the luminescence and the microlens array is arranged in a circular pattern and the pinhole array is arranged in a semi-circular pattern corresponding to approximately one half of the circular pattern of the microlens array.

2. The microscope system of claim 1, wherein the microlens array is arranged on a microlens disk which is adapted to connect to a motor and is configured to rotate.

3. The microscope system of claim 1, further comprising a prism positioned on one side of the microlens array, the prism being configured to transmit the coherent light from the one side of the microlens array to the microlens array toward the sample stage along the beam path of the coherent light, the prism being further configured to receive the luminescence from the microlens array and reflect the luminescence back toward the microlens array.

4. The microscope system of claim 1, wherein the microlens array is attached to a motor and is configured to be shaken while transmitting the coherent light and the luminescence.

5. The microscope system of claim 1, wherein the pinhole array is arranged on a pinhole disk attached to a motor and is configured to rotate.

6. The microscope system of claim 1, wherein the pinhole array is attached to a motor and is configured to be shaken.

7. The microscope system of claim 1, further comprising a dichroic mirror positioned between the microlens array and the pinhole array, the dichroic mirror being configured to receive the coherent light from a direction parallel with a plane of the microlens array and a plane of the pinhole array, and to reflect the coherent light through the microlens array, the dichroic mirror being further configured to transmit the luminescence from the microlens array to the pinhole array.

8. The microscope system of claim 1, wherein the microlens array and the pinhole array are arranged on a common disk.

9. The microscope system of claim 1, wherein the pinhole array and microlens array are oriented on a common disk and contact one another in a layered configuration.

10. The microscope system of claim 1, wherein the beam path of the luminescence passes through only a single microlens array.

11. The microscope system of claim 1, further comprising a motor coupled to the microlens array and configured to move the microlens array with respect to the beam paths of the coherent light and the luminescence.

12. A method for performing super resolution microscopy, comprising:
mounting a sample on a sample stage, the sample having a plurality of probe molecules;
switching on a light source configured to produce a coherent excitation light to cause the coherent light to pass through a microlens array positioned in a beam path extending between the light source and the sample stage;
illuminating the sample with coherent light to cause luminescence from the probe molecules in the sample to pass through the microlens array positioned in a beam path between the sample stage and an image detector and rotating the microlens array while illuminating the sample, and rotating a pinhole array oriented in the beam path between the sample stage and the image detector in synchronization with rotating the microlens array, wherein the microlens array is arranged in a circular pattern and the pinhole array is arranged in a semi-circular pattern
switching the light source off when the pinhole array is rotated in the beam path between the light source and the sample stage and switching the light source on when the pinhole array is rotated out of the beam path between the light source and the sample stage; and
detecting the luminescence from the probe molecules at the image detector.

13. The method of claim 12, further comprising detecting the luminescence from the probe molecules at the image detector when the pinhole array is rotated out of the beam path between the light source and the sample stage.

14. The method of claim 12, further comprising directing the coherent light from the light source toward a dichroic mirror between the microlens array and the pinhole array to be redirected toward the sample stage.

15. The method of claim 12, further comprising detecting the luminescence from the probe molecules at the image detector after the luminescence has passed through both the microlens array and the pinhole array.

16. The method of claim 12, further comprising imaging a modified multi-focal emission pattern of the luminescence onto different sectors of the image detector.

* * * * *